United States Patent
Lee et al.

(10) Patent No.: US 9,883,730 B2
(45) Date of Patent: Feb. 6, 2018

(54) WRIST WEARABLE TERMINAL

(71) Applicant: SAMSUNG ELECTRONICS CO., LTD., Suwon-si (KR)

(72) Inventors: Hyung-sun Lee, Yongin-si (KR); Jun-ho Koh, Suwon-si (KR); Ki-young Kim, Yongin-si (KR); Shin-hee Cho, Suwon-si (KR); Toshikazu Takayanagi, Suwon-si (KR); Doo-woong Lee, Seoul (KR); Youn-ho Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 57 days.

(21) Appl. No.: 14/587,776

(22) Filed: Dec. 31, 2014

(65) Prior Publication Data

US 2015/0189976 A1   Jul. 9, 2015

(30) Foreign Application Priority Data

Jan. 3, 2014   (KR) .................. 10-2014-0000840

(51) Int. Cl.
| | |
|---|---|
| *G06F 1/16* | (2006.01) |
| *A45F 5/00* | (2006.01) |
| *A61B 5/0432* | (2006.01) |
| *A61B 5/00* | (2006.01) |

(52) U.S. Cl.
CPC .............. *A45F 5/00* (2013.01); *A61B 5/0432* (2013.01); *A61B 5/681* (2013.01); *A45F 2005/008* (2013.01); *A45F 2200/0516* (2013.01); *A61B 2560/0209* (2013.01)

(58) Field of Classification Search
CPC ...................................................... A61B 5/681
See application file for complete search history.

(56) References Cited

U.S. PATENT DOCUMENTS

| | | | | |
|---|---|---|---|---|
| 5,280,296 A | * | 1/1994 | Tan ................. | H01Q 7/08 343/718 |
| 5,589,840 A | * | 12/1996 | Fujisawa ........... | H01Q 1/273 343/718 |
| 6,175,729 B1 | * | 1/2001 | He ................... | A44C 5/24 343/718 |
| 6,529,754 B2 | * | 3/2003 | Kondo .............. | A61B 5/02438 600/335 |
| 6,843,771 B2 | * | 1/2005 | Lo .................... | A61B 5/02438 600/459 |
| 7,198,190 B2 | * | 4/2007 | Juhan ............... | G09F 3/005 235/380 |
| 8,073,548 B2 | * | 12/2011 | Colvin, Jr. ........ | A61B 5/076 607/30 |

(Continued)

FOREIGN PATENT DOCUMENTS

KR   10-2010-0072993 A   7/2010

*Primary Examiner* — Anthony Q Edwards
(74) *Attorney, Agent, or Firm* — Sughrue Mion, PLLC (57) ABSTRACT

Provided is a wrist wearable terminal including: a body portion including a function module; a coupling portion fastening the body portion on a wrist; and at least one strap portion linking the body portion and the coupling portion and including at least one function module that is coupled to the function module of the body portion via a signal line to convert or activate a use of at least one function of the wrist wearable terminal depending on a state of wearing of the wrist wearable terminal.

20 Claims, 4 Drawing Sheets

(56) References Cited

U.S. PATENT DOCUMENTS

| | | | |
|---|---|---|---|
| 8,260,405 B2 * | 9/2012 | Aarts | A61B 5/021 600/377 |
| 8,301,211 B2 * | 10/2012 | Lee | H04M 1/274525 340/539.11 |
| 8,604,923 B1 * | 12/2013 | Rivas Alvarez | A61B 5/02055 340/539.12 |
| 8,727,991 B2 * | 5/2014 | Hasegawa-Johnson | A61B 8/02 600/407 |
| 8,784,271 B2 * | 7/2014 | Brumback | A61B 5/0015 340/870.16 |
| 8,947,239 B1 * | 2/2015 | Park | G06K 7/10237 340/539.11 |
| 9,166,276 B2 * | 10/2015 | Chateau | H04B 5/0075 |
| 9,204,798 B2 * | 12/2015 | Proud | H02J 7/025 |
| 9,386,932 B2 * | 7/2016 | Chatterjee | G06F 1/1626 |
| 9,432,091 B2 * | 8/2016 | Proud | H04B 5/0037 |
| 2002/0068873 A1 | 6/2002 | Nissila | |
| 2005/0237704 A1 * | 10/2005 | Ceresoli | G06F 1/163 361/679.03 |
| 2008/0001735 A1 * | 1/2008 | Tran | G06F 19/3418 340/539.22 |
| 2011/0245697 A1 | 10/2011 | Miettinen | |
| 2013/0106603 A1 * | 5/2013 | Weast | G06F 1/163 340/539.11 |
| 2013/0261405 A1 * | 10/2013 | Lee | A61B 5/681 600/301 |
| 2014/0121471 A1 * | 5/2014 | Walker | A61B 5/1128 600/301 |
| 2014/0232328 A1 * | 8/2014 | Pegg | G04C 10/00 320/108 |
| 2014/0257049 A1 * | 9/2014 | Soundarapandian | A61B 5/681 600/301 |
| 2014/0266939 A1 * | 9/2014 | Baringer | H01Q 21/28 343/729 |
| 2014/0306656 A1 * | 10/2014 | Tabata | H01F 38/14 320/108 |
| 2014/0323818 A1 * | 10/2014 | Axelgaard | A61B 5/0022 600/301 |
| 2014/0337621 A1 * | 11/2014 | Nakhimov | G06F 1/163 713/168 |
| 2014/0378794 A1 * | 12/2014 | Conrad | A61B 5/681 600/317 |
| 2015/0173632 A1 * | 6/2015 | Ma | A61B 5/0245 600/324 |
| 2015/0241915 A1 * | 8/2015 | Goyal | G06F 1/16 361/679.03 |
| 2016/0048159 A1 * | 2/2016 | McCormack | G06F 1/163 361/679.03 |
| 2016/0170445 A1 * | 6/2016 | Wai | G06F 1/163 361/679.03 |
| 2017/0071469 A1 * | 3/2017 | Hijazi | A61B 5/0028 |

* cited by examiner

WRIST WEARABLE TERMINAL

CROSS-REFERENCE TO RELATED APPLICATION

This application claims priority from Korean Patent Application No. 10-2014-0000840, filed on Jan. 3, 2014 in the Korean Intellectual Property Office, the disclosure of which is incorporated herein in its entirety by reference.

BACKGROUND

1. Field

Apparatuses and methods consistent with exemplary embodiments relate to a wrist wearable terminal, and more particularly, to a wrist wearable terminal having at least one function module to provide a variety of services to a user.

2. Description of the Related Art

Portable terminals have become more common with modern people and are designed for users to easily carry around. Types of portable terminals may include a wrist wearable type as well as a folder type or a filp type.

It is easy for users to carry around a wrist wearable type portable terminal without risk of loss. However, all functions of the related art wrist worn-type portable terminals are incorporated in a particular portion thereof, i.e., a body portion, which causes interference during the operation of components. In addition, the weight of the terminal is focused to a particular area, thus causing discomfort when wearing.

SUMMARY

Aspects of one or more exemplary embodiments provide a wrist wearable terminal having at least one function module to provide a variety of services to a user.

Additional aspects will be set forth in part in the description which follows and, in part, will be apparent from the description, or may be learned by practice of exemplary embodiments.

According to an aspect of an exemplary embodiment, there is provided a wrist wearable terminal including: a body portion including at least one function module; a coupling portion fastening the body on a wrist; and at least one strap portion linking the body portion and the coupling portion and including at least one function module that is coupled to the at least one function module of the body portion via a signal line to convert a use of at least one function of the wrist wearable terminal depending on a state of wearing.

The coupling portion may include a sensor configured to sense a connected state; and a worn state detector configured to determine the state of wearing when the sensor senses the connected state.

The at least one strap portion may include a device configured to convert or activate a use of the at least one function module of the body portion or the at least one function module of the at least one strap portion depending on the state of wearing sensed from the coupling portion.

The device may include a coil-type electrode integrating an electrode for measuring electrocardiogram and a coil for wireless charging.

The coil-type electrode may be converted to a use of the electrode for measuring electrocardiogram when the coupling portion senses the state of wearing and may be converted to a use of the coil for wireless charging when the coupling portion does not sense the state of wearing.

The at least one strap portion may include a cavity in the at least one strap portion.

The body portion and the at least one strap portion may convert or activate the use of the function depending on the state of wearing sensed by the coupling portion.

According to an aspect of another exemplary embodiment, there is provided a wrist wearable terminal including: a body portion including at least one function module; a coupling portion fastening the body portion on a wrist, and including a function module that is coupled to the at least one function module of the body portion; and the at least one strap portion linking the body portion and the coupling portion and including at least one function module which couples the at least one function module of the body portion to the function module of the coupling portion via a signal line in order to convert a use of at least one function of the wrist wearable terminal depending on a state of wearing.

The coupling portion may include a sensor configured to sense a connected state; and a worn state detector configured to sense the state of wearing when the sensor senses the connected state.

The at least one strap may include a device configured to activate or convert a use of the at least one function module of the body portion or the at least one function module of the at least one strap portion depending on the state of wearing sensed from the coupling portion.

The device may include a coil-type electrode integrating an electrode for measuring electrocardiogram and a coil for wireless charging.

The coil-type electrode may be converted to a use of the electrode for measuring electrocardiogram when the coupling portion senses the state of wearing and may be converted to a use of the coil for wireless charging when the coupling portion does not sense the state of wearing.

According to an aspect of another exemplary embodiment, there is provided a wearable terminal including: a body portion including a first function module; a first functional strap portion connected to a first side of the body portion; a second strap portion connected to a second side of the body portion, opposite the first side; and a coupling portion configured to connect the first strap portion and the second strap portion, wherein the first functional strap portion links the body portion and the coupling portion and includes a second function module, and wherein a use of at least one of the first function module and the second function module is activated according to a state of connection between the first functional strap portion and the second strap portion via the coupling portion.

The wearable terminal may further include a device, included in the body portion, the first functional strap portion, or the second strap portion, configured to convert or activate a use of at least one of the first function module and the second function module depending on the state of connection sensed via the coupling portion.

The wearable terminal may further include a switching portion configured to convert to a use of the first function module or the second function module by connecting the device to the first function module or the second function module when a connection state is sensed via the coupling portion, and to convert to a use of a third function module, comprised in the body portion or the first functional strap portion, by connecting the device to the third function module when the connection state is not sensed via the coupling portion.

The device may include a coil-type electrode integrating an electrode for measuring an electrocardiogram and a coil for wireless charging.

The coil-type electrode may be converted to a use, by the first function module or the second function module, of the electrode for measuring the electrocardiogram when the connected state is sensed and converted to a use, by the third function module, of the coil for wireless charging when the state of wearing is not sensed.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION OF EXEMPLARY EMBODIMENTS

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, exemplary embodiments are merely described below, by referring to the figures, to explain aspects of the present description. As used herein, the term "and/or" includes any and all combinations of one or more of the associated listed items. Furthermore, expressions such as "at least one of," when preceding a list of elements, modify the entire list of elements and do not modify the individual elements of the list.

As the inventive concept allows for various changes and numerous embodiments, particular exemplary embodiments will be illustrated in the drawings and described in detail in the written description. However, this is not intended to limit the inventive concept to particular modes of practice, and it is to be appreciated that all changes, equivalents, and substitutes that do not depart from the spirit and technical scope are encompassed in the inventive concept. In the description, certain detailed explanations of the related art are omitted when it is deemed that they may unnecessarily obscure the essence of the inventive concept.

While such terms as "first," "second," etc., may be used to describe various components, such components may not be limited to the above terms. The above terms are used only to distinguish one component from another.

The terms used in the present specification are merely used to describe particular exemplary embodiments, and are not intended to limit the inventive concept. The terms used to describe exemplary embodiments are selected as general terms used currently as widely as possible regarding functions of elements in exemplary embodiments. However, in specific cases, terms arbitrarily selected by the applicant are also used, and in such cases, the meanings are mentioned in the corresponding detailed description section, so one or more exemplary embodiments should be understood not by literal meanings of the terms but by given meanings of the terms.

An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Figure 1:
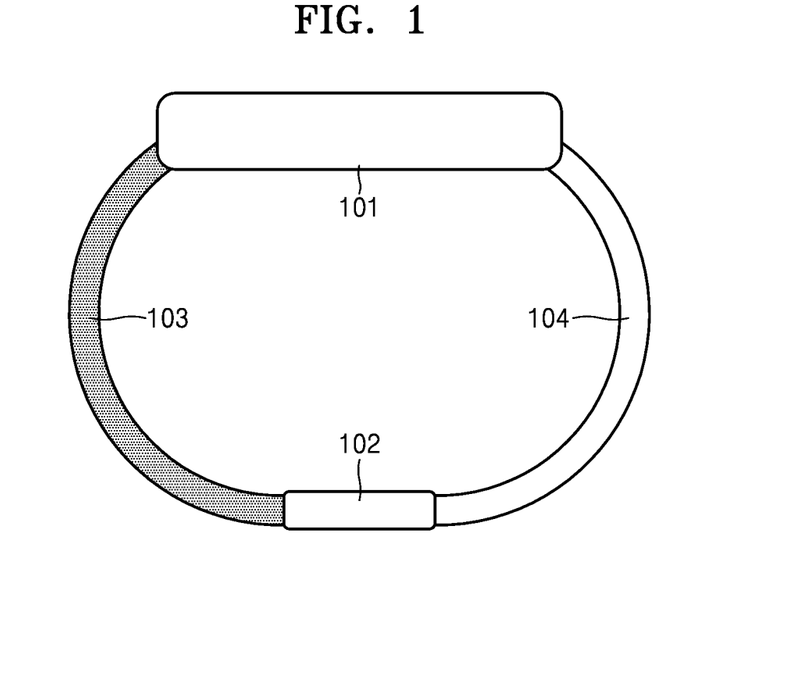
FIG. 1 illustrates a wrist wearable terminal according to an exemplary embodiment.

FIG. 1 illustrates a wrist wearable terminal according to an exemplary embodiment.

The wrist wearable terminal of FIG. 1 may include a body portion 101, a coupling portion 102, a first functional strap portion 103, and a second strap portion 104.

The body portion 101 may include at least one function module (i.e., at least one operation module). A function module implements at least one function (i.e., operation) of the wrist wearable terminal. According to an exemplary embodiment, the at least one function module may have at least one of a display function and a control function, although it is understood that one or more other exemplary embodiments are not limited thereto.

The coupling portion 102 may connect the first functional strap portion 103 and the second strap portion 104 to fasten the body portion 101 on a wrist of a user. Here, the coupling portion 102 may be fixedly or integrally connected to one of the first functional strap portion 103 and the second strap portion 104, and detachably connected to the other of the first functional strap portion 103 and the second strap portion 104. Furthermore, the coupling portion 102 may mechanically, magnetically, etc., connect the first functional strap portion 103 and the second strap portion 104.

The first functional strap portion 103 and the second strap portion 104 may link the body portion 101 and the coupling portion 102.

Furthermore, the first functional strap portion 103 may include at least one function module that is coupled to the at least one function module of the body portion 101 via a signal line to convert or activate a use of the at least one function module of the body portion 101 depending on a state of wearing. According to another exemplary embodiment, at least one function module from among function modules included in the body portion 101 and the first functional strap portion 103 may be activated according to the state of wearing. Furthermore, according to another exemplary embodiment, a control function module or controller that controls an activating or a use converting of at least one function module from among function modules included in the body portion 101 and the first functional strap portion 103 may determine the state of wearing (e.g., based on a sensor signal or information received from the coupling portion 102 or another portion of the wrist wearable terminal) and may control to activate or convert a use of the at least one function module from among function modules included in the body portion 101 and the first functional strap portion 103 accordingly. In this case, the control function module or controller may be included in the body portion 101 or another portion of the wrist wearable terminal.

The first functional strap portion 103 not only mechanically links the body portion 101 and the coupling portion 102, but also has electrical elements therein to transmit electrical signals. Additionally, the first functional strap portion 103 further includes a function module or device that converts or activates a use of the at least one function module of the body portion 101 depending on the state of wearing that is detected by a sensor, e.g., a sensor in the coupling portion 102 or another portion of the wrist wearable terminal. Here, the sensor may detect whether the first functional strap portion 103 and the second strap portion 104 are connected to each other, or whether one of the first functional strap portion 103 and the second strap portion 104 is connected to the coupling portion 102.

By way of example, when the state of wearing is detected or determined, the first functional strap portion 103 converts or activates a use of the at least one function module of the body portion 101 to an electrocardiogram (ECG) measuring function module, and when the state of wearing is not detected or determined, the first functional strap portion 103 converts or activates a use of the at least one function module of the body portion 101 to a wireless charging function module. According to an exemplary embodiment, the first functional strap portion 103 may be formed of or include a material that may be easily processed, such as rubber or urethane, though it is understood that one or more other exemplary embodiments are not limited thereto. If the first functional strap portion 103 is formed of urethane, the first functional strap portion 103 may be manufactured by using a double-shot injection molding process, after inserting an electronic circuit or electronic component in a mold. According to another exemplary embodiment, the first functional strap portion 103 may include or be formed to have a cavity therein so that an electronic circuit or electronic component for the at least one function module may be inserted in a post-manufacturing process.

In case that the wrist wearable terminal has a wireless charging function, and all function modules for the wireless charging function module are mounted in the body portion 101, the exterior of the body portion 101 may not be formed of a metallic material to prevent interference of a coil to be used for power transmission. According to an exemplary embodiment, however, in case that a flexible printed circuit board having a coil is inserted to the first functional strap portion 103, and the flexible printed circuit board is electrically linked to the body portion 101, the body portion 101 may not have interference by transmission of power signals even when the body portion 101 is manufactured using a metallic material.

Figure 2:
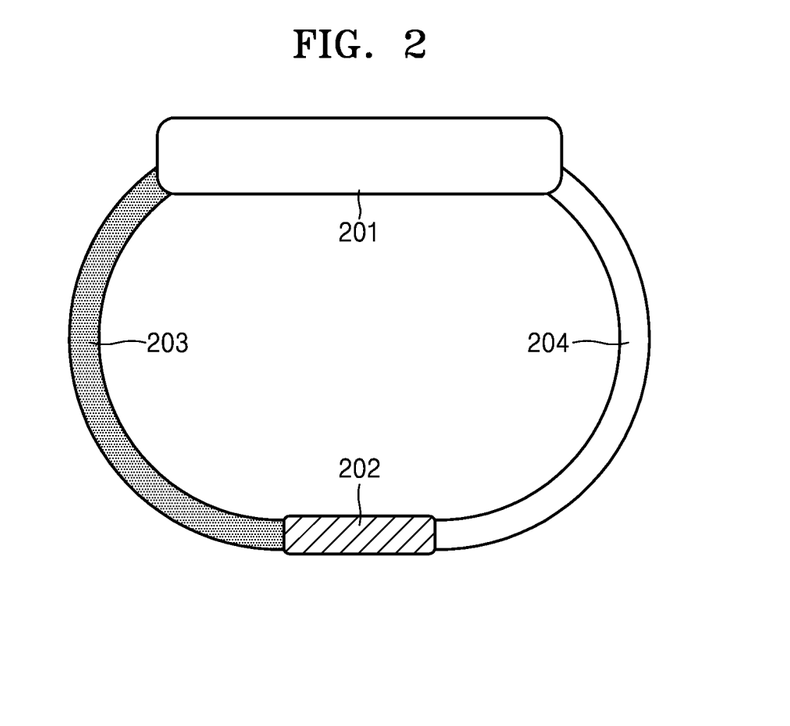
FIG. 2 illustrates a wrist wearable terminal according to another exemplary embodiment.

FIG. 2 illustrates a wrist wearable terminal according to another exemplary embodiment.

The wrist wearable terminal of FIG. 2 may include a body portion 201, a functional coupling portion 202, a first functional strap portion 203, and a second strap portion 204.

The body portion 201 may include at least one function module. According to an exemplary embodiment, the at least one function module may have at least one of a display function and a control function, although it is understood that one or more other exemplary embodiments are not limited thereto.

The functional coupling portion 202 may connect the first functional strap portion 203 and the second strap portion 204 to fasten the body portion 201 on a wrist of a user. Furthermore, the functional coupling portion 202 may include at least one function module that is coupled to at least one function module of the body portion 201. That is, the functional coupling portion 202 may include electrical circuitry or an electrical circuit module therein in order to perform at least one of signal processing, one or more operations, storing, and communication.

The first functional strap portion 203 and the second strap portion 204 may link the body portion 201 and the functional coupling portion 202.

The first functional strap portion 203 may include at least one function module which may be coupled to the at least one function module of the body portion 201 via a signal line to convert or activate a use of the at least one function module of the body portion 201 depending on a state of wearing. According to another exemplary embodiment, at least one function module from among function modules included in the body portion 201, the first functional strap portion 203, and/or the coupling portion 202 may be activated according to the state of wearing. Furthermore, according to another exemplary embodiment, a control function module or controller that controls an activating or a use converting of at least one function module from among function modules included in the body portion 201, the first functional strap portion 203, and/or the coupling portion 202 may determine the state of wearing (e.g., based on a sensor signal or information received from the coupling portion 202 or another portion of the wrist wearable terminal) and may control to activate or convert a use of the at least one function module from among function modules included in the body portion 201, the first functional strap portion 203, and/or the coupling portion 202 accordingly. In this case, the control function module or controller may be included in the body portion 201 or another portion of the wrist wearable terminal.

The first functional strap portion 203 not only mechanically links the body portion 201 and the coupling portion 202, but also has electrical elements therein to transmit electrical signals. Additionally, the first functional strap portion 203 further includes a function module or device that converts or activates a use of the at least one function module of the body portion 201 depending on the state of wearing that is detected by a sensor in the coupling portion 202 or another portion of the wrist wearable terminal. For example, when the state of wearing is detected, the first functional strap portion 203 converts or activates a use of the at least one function module of the body portion 201 to an ECG measuring function module, and when the state of wearing is not detected, the first functional strap portion 203 converts or activates a use of the at least one function module of the body portion 201 to a wireless charging function module. According to an exemplary embodiment, the first functional strap portion 203 may be formed of or include a material that is easily processed, such as rubber or urethane, though it is understood that one or more other exemplary embodiments are not limited thereto. According to another exemplary embodiment, the first functional strap portion 203 may include or be formed to have a cavity therein so that an electronic circuit or electronic component for the at least one function module may be inserted in a post-manufacturing process.

According to an exemplary embodiment, when the functional coupling portion 202 includes circuits and electrodes for measuring ECG, and the first functional strap portion 203 includes a signal line electrically linking the body portion 201 and the functional coupling portion 202, a volume and weight of the functional coupling portion 202 of the wrist wearable terminal may increase. However, a volume and weight of the body portion 201 may decrease so as to achieve overall weight balance, and the body 201 portion may be freely designed since the electrode for measuring EGC is disposed under the wrist.

Figure 3:
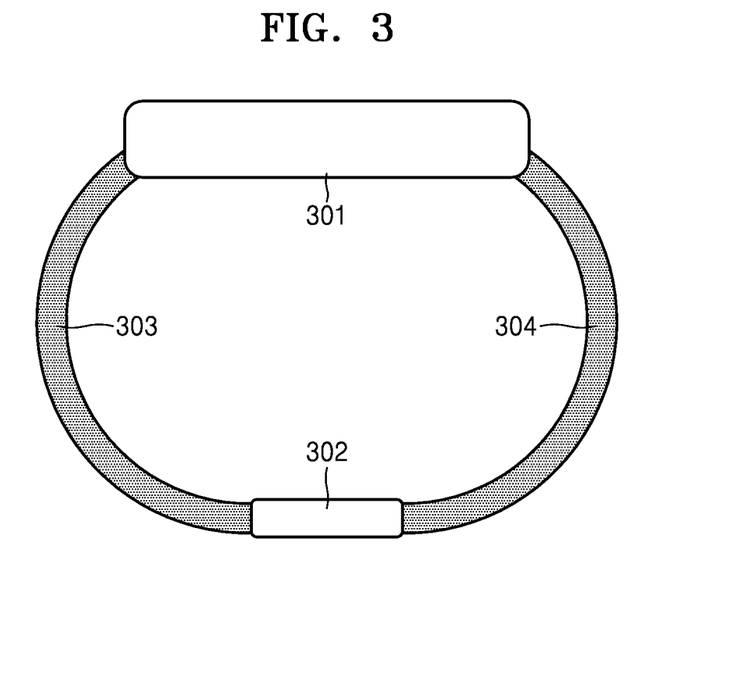
FIG. 3 illustrates a wrist wearable terminal according to another exemplary embodiment.

FIG. 3 illustrates a wrist wearable terminal according to another exemplary embodiment.

The wrist wearable terminal of FIG. 3 may include a body portion 301, a coupling portion 302, a first functional strap portion 303, and a second functional strap portion 304.

The body portion 301 may include at least one function module. According to an exemplary embodiment, the at least one function module may have at least one of a display function and a control function, though it is understood that one or more other exemplary embodiments are not limited thereto.

The coupling portion 302 may connect the first functional strap portion 303 and the second functional strap portion 304 to fasten the body portion 301 on a wrist of a user.

The first functional strap portion 303 and the second functional strap portion 304 may link the body portion 301 and the coupling portion 302.

The first functional strap portion 303 may include at least one function module which may be coupled to the at least one function module of the body portion 301 via a signal line to convert or activate a use of the at least one function module of the body portion 301 depending on a state of wearing. According to another exemplary embodiment, at least one function module from among function modules included in the body portion 301, the first functional strap portion 303, and/or the second functional strap portion 304 may be activated according to the state of wearing. Furthermore, according to another exemplary embodiment, a control function module or controller that controls an activating or a use converting of at least one function module from among function modules included in the body portion 301, the first functional strap portion 303, and/or the second functional strap portion 304 may determine the state of wearing (e.g., based on a sensor signal or information received from the coupling portion 302 or another portion of the wrist wearable terminal) and may control to activate or convert a use of the at least one function module from among function modules included in the body portion 301, the first functional strap portion 303, and/or the second functional strap portion 304 accordingly. In this case, the control function module or controller may be included in the body portion 201 or another portion of the wrist wearable terminal.

The first functional strap portion 303 not only mechanically links the body portion 301 and the coupling portion 302, but also has electrical elements therein to transmit electrical signals. Additionally, the first functional strap portion 303 further includes a function module or device that converts or activates a use of the at least one function module of the body portion 301 depending on the state of wearing that is detected by a sensor in the coupling portion 302 or another portion of the wrist wearable terminal. For example, when the state of wearing is detected, the first functional strap 303 converts or activates a use of the at least one function module of the body portion 301 to an ECG measuring function module, and when the state of wearing is not detected, the first functional strap portion 303 converts or activates a use of the at least one function module of the body portion 301 to a wireless charging function module. According to an exemplary embodiment, the first functional strap portion 303 may be formed of or include a material that is easily processed, such as rubber or urethane, though it is understood that one or more other exemplary embodiments are not limited thereto. According to another exemplary embodiment, the first functional strap portion 303 may include or be formed to have a cavity therein so that an electronic circuit or electronic component for the at least one function module may be inserted in a post-manufacturing process.

The second functional strap portion 304 may include at least one function module which may be coupled to the at least one function module of the body portion 301 via a signal line to convert or activate a use of the at least one function module of the body portion 301 depending on a state of wearing. According to another exemplary embodiment, at least one function module from among function modules included in the body portion 301, the first functional strap portion 303, and/or the second functional strap portion 304 may be activated according to the state of wearing.

The second functional strap portion 304 not only mechanically links the body portion 301 and the coupling portion 302, but also has electrical elements therein to transmit electrical signals. Additionally, the second functional strap portion 304 further includes a function module or device that converts or activates a use of the at least one function module of the body portion 301 depending on the state of wearing that is detected by a sensor. According to an exemplary embodiment, the second functional strap portion 304 may be formed of or include a material that is easily processed, such as rubber or urethane, though it is understood that one or more other exemplary embodiments are not limited thereto. According to another exemplary embodiment, the second functional strap portion 304 may include or be formed to have a cavity therein so that an electronic circuit or electronic component for the at least one function module may be inserted in a post-manufacturing process.

An example of using the first functional strap portion 303 and the second functional strap portion 304 may be a wrist wearable terminal having an ECG measuring function and a wireless charging function. ECG measurement utilizes at least two electrodes each in contact with a left side and a right side of a body relative to the heart. One electrode may be mounted on a surface of the body portion 301, wherein the surface is in contact with the wrist, and another electrode may be mounted on an outer surface of the first functional strap portion 303 or the second functional strap portion 304, and the first functional strap portion 303 or the second functional strap portion 304 is positioned close to the body to measure ECG. Also, since a coil for wireless charging is affected by adjacent metal, performance of the coil may degrade when the coil and the electrode for ECG measurement is embedded in the same strap. Hence, the coil for wireless charging may be embedded in the first functional strap portion 303 or the second functional strap portion 304 which is positioned far from the body.

Figure 4:
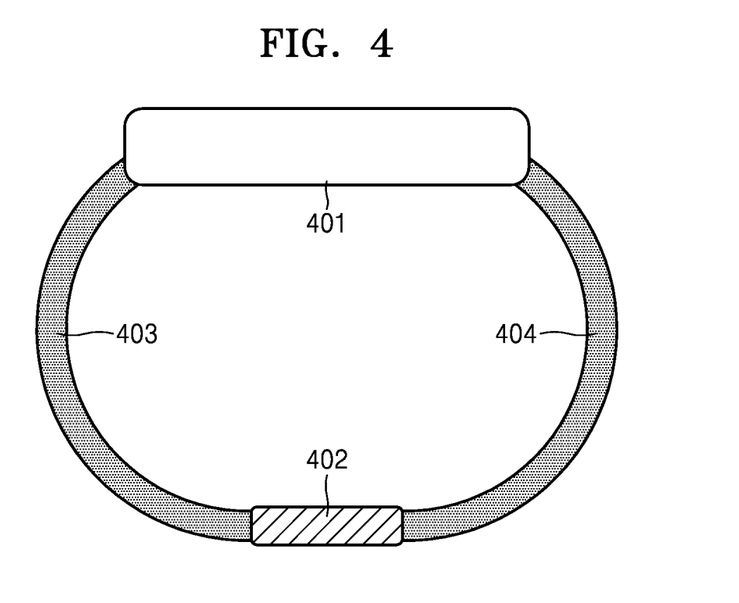
FIG. 4 illustrates a wrist wearable terminal according to another exemplary embodiment.

FIG. 4 illustrates a wrist wearable terminal according to another exemplary embodiment.

The wrist wearable terminal of FIG. 4 may include a body portion 401, a functional coupling portion 402, a first functional strap portion 403, and a second functional strap portion 404.

The body portion 401 may include at least one function module. According to an exemplary embodiment, the at least one function module may have at least one of a display function and a control function, though it is understood that one or more other exemplary embodiments are not limited thereto.

The functional coupling portion 402 may connect the first functional strap portion 403 and second functional strap portion 404 to fasten the body portion 401 on a wrist of a user.

The first functional strap portion 403 and the second functional strap portion 404 may link the body portion 401 and the functional coupling portion 402.

The first functional strap portion 403 may include at least one function module which may be coupled to the at least one function module of the body portion 401 via a signal line to convert or activate a use of the at least one function module of the body portion 401 depending on a state of wearing. According to another exemplary embodiment, at least one function module from among function modules included in the body portion 401, the first functional strap portion 403, the second functional strap portion 404, and/or the coupling portion 402 may be activated according to the state of wearing. Furthermore, according to another exemplary embodiment, a control function module or controller that controls an activating or a use converting of at least one function module from among function modules included in the body portion 401, the first functional strap portion 403, the second functional strap portion 404, and/or the coupling portion 402 may determine the state of wearing (e.g., based on a sensor signal or information received from the coupling portion 402 or another portion of the wrist wearable terminal) and may control to activate or convert a use of the at least one function module from among function modules included in the body portion 401, the first functional strap portion 403, the second functional strap portion 404, and/or the coupling portion 402 accordingly. In this case, the control function module or controller may be included in the body portion 401 or another portion of the wrist wearable terminal.

The first functional strap portion 403 not only mechanically links the body portion 401 and the coupling portion 402, but also has electrical elements therein to transmit electrical signals. Additionally, the first functional strap portion 403 further includes a module or device that converts or activates a use of the at least one function module of the body portion 401 depending on the state of wearing that is detected by a sensor in the coupling portion 402 or another portion of the wrist wearable terminal. For example, when the state of wearing is detected, the first functional strap portion 403 converts or activates a use of the at least one function module of the body portion 401 to an ECG measuring function module, and when the state of wearing is not detected, the first functional strap portion 403 converts or activates a use of the at least function module of the body portion 401 to a wireless charging function module. According to an exemplary embodiment, the first functional strap portion 403 may be formed of or include a material that is easily processed, such as rubber or urethane, though it is understood that one or more other exemplary embodiments are not limited thereto. According to an exemplary embodiment, the first functional strap portion 403 may include or be formed to have a cavity therein for an electronic circuit or electronic component for the at least one function module to be inserted in a post-processing.

The second functional strap portion 404 may include at least one function module that may be coupled to the at least one function module of the body portion 401 via a signal line to convert or activate a use of the at least one function module of the body portion 401 depending on a state of wearing. Additionally, the second functional strap portion 404 further includes a device that may convert or activate a use of the at least one function module of the body portion 401 depending on the state of wearing. According to another exemplary embodiment, at least one function module from among function modules included in the body portion 401, the first functional strap portion 403, the second functional strap portion 3404, and/or the coupling portion 402 may be activated according to the state of wearing.

According to an exemplary embodiment, the second functional strap portion 404 may be formed of or include a material that is easily processed, such as rubber or urethane, though it is understood that one or more other exemplary embodiments are not limited thereto. According to an exemplary embodiment, the second functional strap portion 404 may include or be formed to have a cavity therein for an electronic circuit or electronic component for the at least one function module to be inserted in a post-processing.

An example of using the functional coupling portion 402, the first functional strap portion 403, and the second functional strap portion 404 may be a wrist wearable terminal having an ECG measuring function and a wireless charging function.

The functional coupling portion 402 may include circuits and electrodes for measuring ECG, and the functional coupling portion 402 and/or the first functional strap portion 403 may include a signal line for linking the circuits and electrodes for measuring ECG and the body portion 401. Hence, the wrist wearable terminal may have a decreased weight in the body portion 401, and thus have an improved overall feeling of wearing and degree of freedom in design by using the functional coupling portion 402, the first functional strap portion 403, and the second functional strap portion 404. Also, since a coil for wireless charging is under the influence of adjacent metal, the coil for wireless charging may be embedded in the second functional strap portion 404 that is opposite to the first functional strap portion 403, which may include the signal line for linking.

Figure 5:
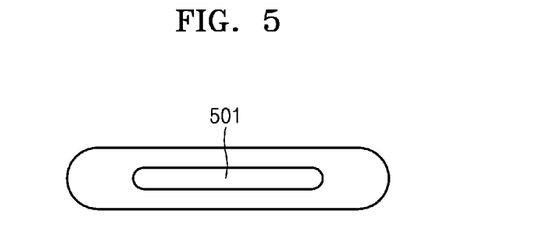
FIG. 5 is a cross-sectional view of a first functional strap and/or a second strap shown in FIGS. 1 to 4.

FIG. 5 is a cross-sectional view of a first functional strap portion and/or a second strap portion shown in FIGS. 1 to 4;

Referring to FIG. 5, the first functional strap portion and the second functional strap portion may include or be formed to have a cavity 501 therein for an electronic circuit or electronic component for a function module to be inserted.

Figure 6:
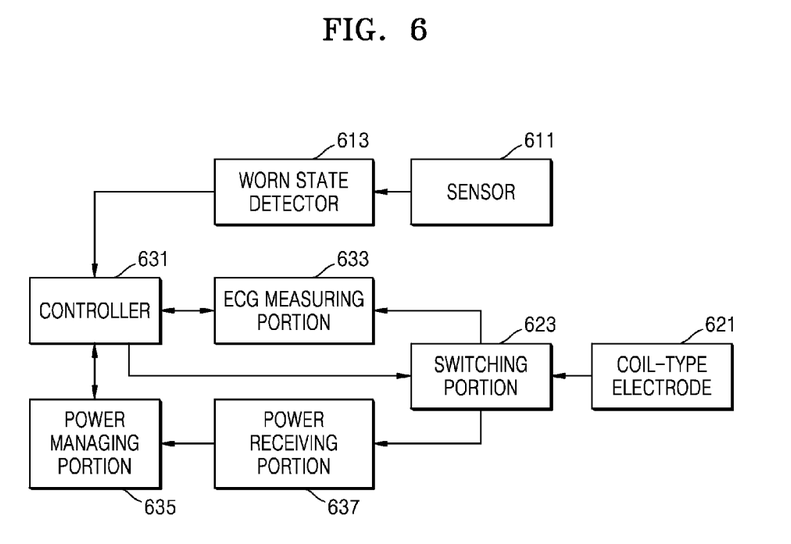
FIG. 6 illustrates function modules embedded in the wrist wearable terminals of FIGS. 1 to 4.

FIG. 6 illustrates function modules embedded in the wrist wearable terminals of FIGS. 1 to 4.

FIG. 6 illustrates function modules that may be intelligently converted to or activated in the wrist wearable terminal depending on a circumstance or event. For example, the wrist wearable terminal may have an ECG measuring function and a wireless charging function depending on a state of wearing. That is, when the wrist wearable terminal is worn on a wrist, the wrist wearable terminal provides an ECG measuring function, and when the wrist wearable terminal is not worn on a wrist, the wrist wearable terminal provides a wireless charging function.

Furthermore, according to one or more exemplary embodiments, the wrist wearable terminal may have functions that vary depending on whether the wrist wearable terminal is in indoors or outdoors, a time of day, a time of year, a calendar event, a communication event, an event in a connected device (e.g., a communication event or an application event in a connected host device, a connected portable device, a connected mobile phone, etc.), a detected biometric event, etc.

Referring to FIG. 6, the wrist wearable terminal having an ECG measuring function and a wireless charging function may have a sensor 611, a worn state detector 613, a coil-type electrode 621, a switching portion 623, a controller 631, an ECG measuring portion 633, a power managing portion 635, and a power receiving portion 637.

The sensor 611 and the worn state detector 613 may be embedded in the functional coupling portion 202, 402.

The coil-type electrode 621 and the switching portion 623 may be embedded in the first functional strap portion 103, 203, 303, 403 and/or second functional strap portion 304, 404.

The controller 631, the ECG measuring portion 633, the power managing portion 635, and the power receiving portion 637 may be embedded in the body portion 101, 201, 301, 401, the functional coupling portion 202, 402, the first functional strap portion 103, 203, 303, 403, and/or the second functional strap portion 304, 404.

Referring to FIG. 6, the sensor 611 may sense a connected state of two straps or strap portions, e.g., a connected state of the two straps or strap portions via a coupling portion. According to an exemplary embodiment, the sensor 611 may be a hook sensor, though it is understood that one or more other exemplary embodiments are not limited thereto. For example, according to another exemplary embodiment, two small electrodes may be mounted on a surface, which is in contact with a wrist, so that the connected state may be sensed through variation in electrical resistance when the two small electrodes are in contact with skin.

The worn state detector 613 may sense a state of wearing when the sensor 611 senses the connected state.

The coil-type electrode 621 may be an integrated device of an electrode for ECG measurement and a coil for wireless charging. The coil-type electrode 621 may be a device to convert a use of at least one function module, for example, from an ECG measuring function to a wireless charging function, depending on the state of wearing sensed from the coupling portion 202, 402.

The controller 631 may transmit a signal corresponding to a state of wearing detected by the worn state detector 613 to the switching portion 623 and control an ECG measuring function of the ECG measuring portion 633 and a wireless charging function of the power managing portion 635.

The switching portion 623 may convert to either the ECG measuring function by linking or connecting the coil-type electrode 621 to the ECG measuring portion 633 (e.g., an ECG measuring function module) or the wireless charging function by linking the coil-type electrode 621 to the power receiving portion 637 (e.g., a wireless charging function module or a power receiving function module) depending on the state of wearing.

The ECG measuring portion 633 may measure ECG by using bio-signals output from the coil-type electrode 621 via the switching portion 623.

The power receiving portion 637 may receive power output from the coil-type electrode 621 via the switching portion 623.

The power managing portion 635 may perform a wireless charging function by using power received from the power receiving portion 637.

Figure 7:
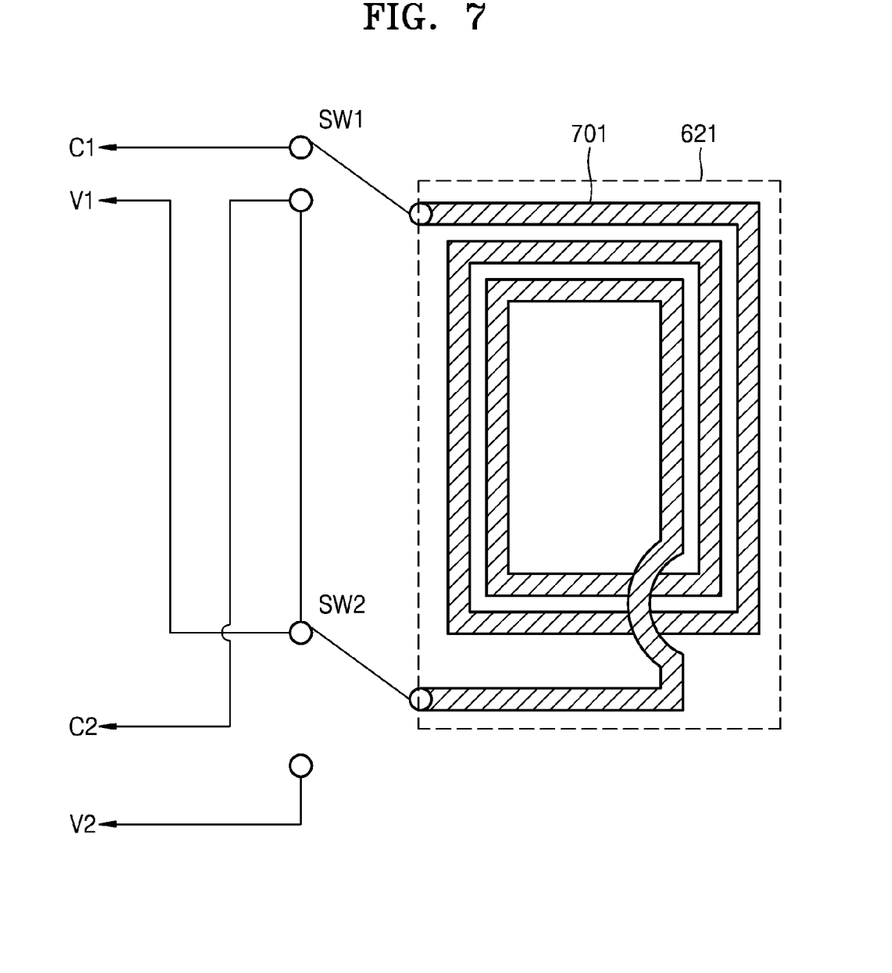
FIG. 7 illustrates a switching portion and a coil-type electrode shown in FIG. 6.

FIG. 7 illustrates the switching portion 623 and a coil-type electrode 621 shown in FIG. 6.

Referring to FIG. 7, the coil-type electrode 621 may have a loop shape 701 and high inductance for a frequency band of power signals used for wireless charging, but have low inductance for bio-signals having low frequency such as ECG, similar to general signal lines. The coil-type electrode 621 may be linked either to the ECG measuring portion 633 V1, V2 or to the power receiving portion 637 C1, C2 by a switch SW1, SW2 depending on the state of wearing.

While exemplary embodiments have been described above with reference to a wrist wearable terminal, it is understood that one or more other exemplary embodiments are not limited thereto and may be implemented, for example, as an ankle wearable terminal, a necklace terminal, a wearable terminal, etc.

According to an exemplary embodiment, the wrist wearable terminal may distribute its weight to improve a degree of freedom in design and an overall feeling of wearing. In addition, the wrist wearable terminal may perform functions such as bio-signal measurement at various sites on the wrist. Also, because the function module that is likely to be interfered by a metal material is isolated, operations of the wrist wearable terminal may not be interfered with even if the wrist wearable terminal is designed using various materials such as metal. According to an exemplary embodiment, the wrist wearable terminal may take advantage of converting a use of a device, such as an unused antenna, to a use as an electrode for measuring bio-signals, according to the state of a user.

In addition, one or more exemplary embodiments can also be implemented through computer readable code/instructions in/on a medium, e.g., a computer readable medium, to control at least one processing element to implement any above-described exemplary embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored/transferred and executed in a distributed fashion. Furthermore, the processing element could include a processor or a computer processor, and processing elements may be distributed and/or included in a single device. Additionally, it is understood that the above-described modules may be implemented as hardware (e.g., a processor, a memory, etc.), software (e.g., software implemented by a processing element), or a combination of hardware and software.

It should be understood that exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept(s) as defined by the following claims.

What is claimed is:

1. A wrist wearable terminal comprising:
a body portion comprising a function module for performing a first function and a second function;
a coupling portion configured to fasten the body portion on a wrist; and
at least one strap portion, the strap portion linking the body portion and the coupling portion, the at least one strap portion comprising a signal line, and a function module that is coupled to the function module of the body portion via the signal line and performs a switching operation with regard to the first function and the second function of the body portion depending on a wearing state of the wrist wearable terminal, wherein the first function is different from the second function.

2. The wrist wearable terminal of claim 1, wherein the coupling portion comprises:
a sensor configured to sense a connected state of a first strap portion and a second strap portion, among the at least one strap portion; and
a worn state detector configured to determine the wearing state when the sensor senses the connected state.

3. The wrist wearable terminal of claim 1, wherein the at least one strap portion comprises a device configured to convert or activate a use of the the function module of the body portion or the function module of the at least one strap portion depending on the wearing state sensed via the coupling portion.

4. The wrist wearable terminal of claim 3, wherein the device comprises a coil-type electrode integrating an electrode for measuring an electrocardiogram and a coil for wireless charging.

5. The wrist wearable terminal of claim 4, wherein the coil-type electrode is converted to a use of the electrode for measuring the electrocardiogram when the state of wearing is sensed and is converted to a use of the coil for wireless charging when the wearing state is not sensed.

6. The wrist wearable terminal of claim 5, further comprising a switching portion configured to convert to a use of an electrocardiogram measuring function module by connecting the coil-type electrode to the electrocardiogram measuring function module when the wearing state is sensed, and to convert to a use of a wireless charging function module by connecting the coil-type electrode to the wireless charging function module when the wearing state is not sensed.

7. The wrist wearable terminal of claim 1, wherein the at least one strap portion comprises a cavity in the at least one strap portion, the cavity including at least one of an electronic circuit and an electronic component for the function module of the at least one strap portion.

8. The wrist wearable terminal of claim 1, wherein the body portion and the at least one strap portion convert or activate the use of the at least function depending on the wearing state sensed by the coupling portion.

9. The wrist wearable terminal of claim 1, wherein:
the at least one strap portion comprises a first functional strap portion on a first side of the coupling portion and a second strap portion on a second side of the coupling portion; and
the first functional strap portion comprises the function module of the at least one strap portion, and the second strap portion does not include a function module.

10. The wrist wearable terminal of claim 1, wherein:
the at least one strap portion comprises a first functional strap portion on a first side of the coupling portion and a second functional strap portion on a second side of the coupling portion; and
the first functional strap portion comprises at least one function module, and the second functional strap portion comprises at least one function module.

11. A wrist wearable terminal comprising:
a body portion comprising a function module for performing a first function and a second function;
a coupling portion configured to fasten the body portion on a wrist, and comprising a function module that is coupled to the function module of the body portion; and
at least one strap portion, the strap portion linking the body portion, the at least one strap portion comprising a signal line, and a function module that couples the function module of the body portion to the function module of the coupling portion via the signal line and performs a switching operation with regard to the first function and the second function of the body portion depending on a wearing state of the wrist wearable terminal, wherein the first function is different from the second function.

12. The wrist wearable terminal of claim 11, wherein the coupling portion comprises:
a sensor configured to sense a connected state of a first strap portion and a second strap portion, among the at least one strap portion; and
a worn state detector configured to determine the wearing state when the sensor senses the connected state.

13. The wrist wearable terminal of claim 11, wherein the at least one strap portion comprises a device configured to convert or activate a use of the function module of the body portion, the function module of the at least one strap portion, and the function module of the coupling portion depending on the wearing state sensed from the coupling portion.

14. The wrist wearable terminal of claim 13, wherein the device comprises a coil-type electrode integrating an electrode for measuring an electrocardiogram and a coil for wireless charging.

15. The wrist wearable terminal of claim 14, wherein the coil-type electrode is converted to a use of the electrode for measuring the electrocardiogram when the coupling portion senses the state of wearing and is converted to a use of the coil for wireless charging when the coupling portion does not sense the state of wearing.

16. The wrist wearable terminal of claim 11, wherein:
the at least one strap portion comprises a first functional strap portion on a first side of the coupling portion and a second strap portion on a second side of the coupling portion; and
the first functional strap portion comprises the at least one function module of the at least one strap portion, and the second strap portion does not include a function module.

17. The wrist wearable terminal of claim 11, wherein:
the at least one strap portion comprises a first functional strap portion on a first side of the coupling portion and a second functional strap portion on a second side of the coupling portion; and
the first functional strap portion comprises at least one function module, and the second functional strap portion comprises at least one function module.

18. A wearable terminal comprising:
a body portion comprising a first function module for performing a first function and a second function;
a first functional strap portion connected to a first side of the body portion;
a second strap portion connected to a second side of the body portion, opposite the first side; and
a coupling portion configured to connect the first strap portion and the second strap portion,
wherein the first functional strap portion links the body portion and the coupling portion and comprises a second function module, and
wherein the second function module performs a switching operation with regard to the first function and the second function of the body portion according to a state of connection between the first functional strap portion and the second strap portion via the coupling portion.

19. The wearable terminal of claim 18, further comprising a device, included in the body portion, the first functional strap portion, or the second strap portion, configured to convert or activate a use of at least one of the first function module and the second function module depending on the state of connection sensed via the coupling portion.

20. The wearable terminal of claim 19, further comprising a switching portion configured to convert to a use of the first function module or the second function module by connecting the device to the first function module or the second function module when a connection state is sensed via the coupling portion, and to convert to a use of a third function module, comprised in the body portion or the first functional strap portion, by connecting the device to the third function module when the connection state is not sensed via the coupling portion.

* * * * *